United States Patent
Canas et al.

(10) Patent No.: US 8,828,208 B2
(45) Date of Patent: Sep. 9, 2014

(54) LIPID BILAYER SENSOR ARRAY

(75) Inventors: Antonio Canas, New Malden (GB); Simon Adrian Wells, Weston Turville (GB)

(73) Assignee: Oxford Nanopore Technologies Limited, Oxford (GB)

(*) Notice: Subject to any disclaimer, the term of this patent is extended or adjusted under 35 U.S.C. 154(b) by 335 days.

(21) Appl. No.: 13/265,448

(22) PCT Filed: Apr. 19, 2010

(86) PCT No.: PCT/GB2010/000789
§ 371 (c)(1),
(2), (4) Date: Feb. 10, 2012

(87) PCT Pub. No.: WO2010/122293
PCT Pub. Date: Oct. 28, 2010

(65) Prior Publication Data
US 2012/0133354 A1    May 31, 2012

Related U.S. Application Data

(60) Provisional application No. 61/170,729, filed on Apr. 20, 2009.

(51) Int. Cl.
*G01N 33/53* (2006.01)
*G01N 27/327* (2006.01)

(52) U.S. Cl.
CPC .............. *G01N 33/53* (2013.01); *G01N 27/3272* (2013.01)
USPC .......... 204/450; 204/400; 204/600; 422/68.1; 422/82.01; 435/287.1; 205/775

(58) Field of Classification Search
CPC ........................... G01N 33/53; G01N 27/3272
USPC .......... 204/400, 450, 600; 205/775; 422/68.1, 422/82.01; 435/287.1
See application file for complete search history.

(56) References Cited

U.S. PATENT DOCUMENTS 4,659,920 A    4/1987 Nishiura et al.
5,694,495 A    12/1997 Hara et al.
(Continued)

FOREIGN PATENT DOCUMENTS

EP    1 965 210    *    8/2008
EP    1965210 A1    9/2008
(Continued)

OTHER PUBLICATIONS

Japanese Office Action for Application No. 2012-506560, 9 pages, dated May 2, 2014.
(Continued)

*Primary Examiner* — Jennifer Dieterle
(74) *Attorney, Agent, or Firm* — Nelson Mullins Riley & Scarborough LLP; Anthony A. Laurentano; Jane E. Remillard, Esq.

(57) ABSTRACT

An apparatus for sensing of an interaction of a molecular entity with a membrane protein in a lipid bilayer comprises an array of sensor elements (21) arranged to output an electrical signal that is dependant on occurrences of the interaction. A detection circuit (3) comprised detection channels (30) capable of amplifying an electrical signal from a sensor element. More sensor elements (21) are provided than detection channels (30), and detection channels (30) are selectively connected to sensor elements (21) that have acceptable quality of performance in that a lipid bilayer is formed and that an acceptable number of membrane proteins are inserted, on the basis of the amplified electrical signals that are output from the detection channels. This improves the efficiency of utilization of the detection channels, due to inefficiency in the utilization of the sensor elements, resulting in a reduction in the cost of the apparatus and the ability to perform sensing using relatively small samples.

20 Claims, 4 Drawing Sheets

(56) References Cited

U.S. PATENT DOCUMENTS

| | | |
|---|---|---|
| 7,001,792 B2 | 2/2006 | Sauer et al. |
| 2003/0070923 A1* | 4/2003 | Schroeder et al. ............ 204/400 |
| 2004/0040868 A1 | 3/2004 | DeNuzzio et al. |
| 2004/0055901 A1* | 3/2004 | Petersen et al. ............... 205/789 |
| 2007/0095671 A1 | 5/2007 | Kovacs |
| 2009/0167288 A1* | 7/2009 | Reid et al. ....................... 324/72 |

FOREIGN PATENT DOCUMENTS

| | | |
|---|---|---|
| WO | 98/01758 A1 | 1/1998 |
| WO | 02/29402 A2 | 4/2002 |
| WO | 2008/042018 A2 | 4/2008 |
| WO | 2008/102120 A1 | 8/2008 |
| WO | 2009/077734 A2 | 6/2009 |

OTHER PUBLICATIONS

Audet, Yves et al., "Yield Improvement of a Large Area Magnetic Field Sensor Array Using Redundancy Schemes," IEEE Transactions on Very Large Scale Integration (VLSI) Systems, vol. 5(1):28-33 (1997).

Zagnoni, M. et al., "Microfluidic array platform for simultaneous lipid bilayer membrane formation," Biosensors and Bioelectronics, vol. 24:1235-1240 (2009).

Statement of Facts & Arguments, Opposition against EP 2422198 B1, European Patent Application 10716404.8, 10 pages, dated Jul. 7, 2014.

* cited by examiner

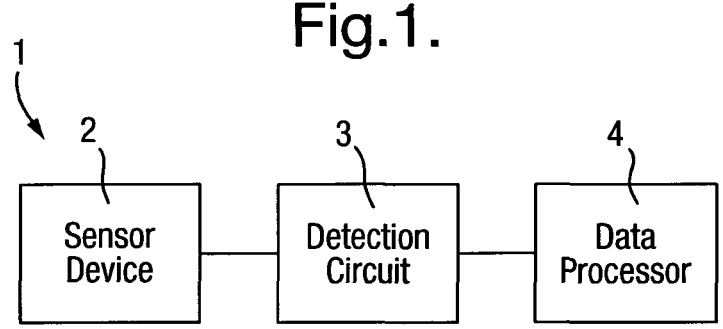
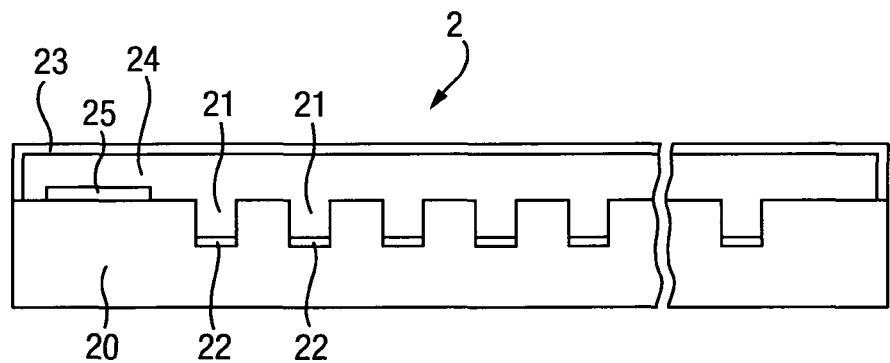

Fig.7.
Fig.8.
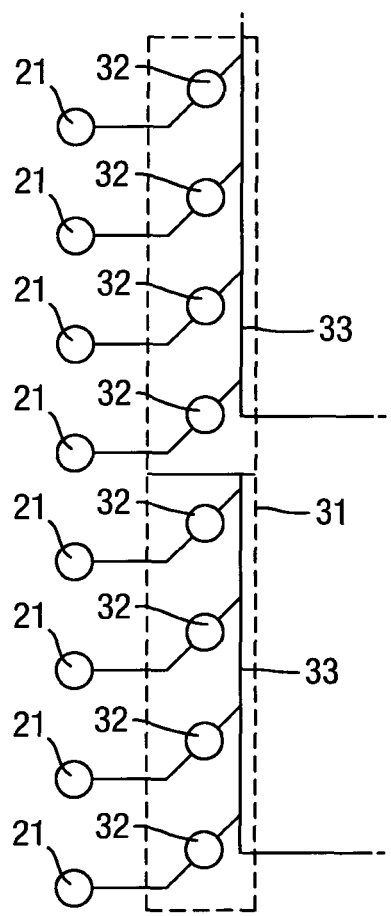
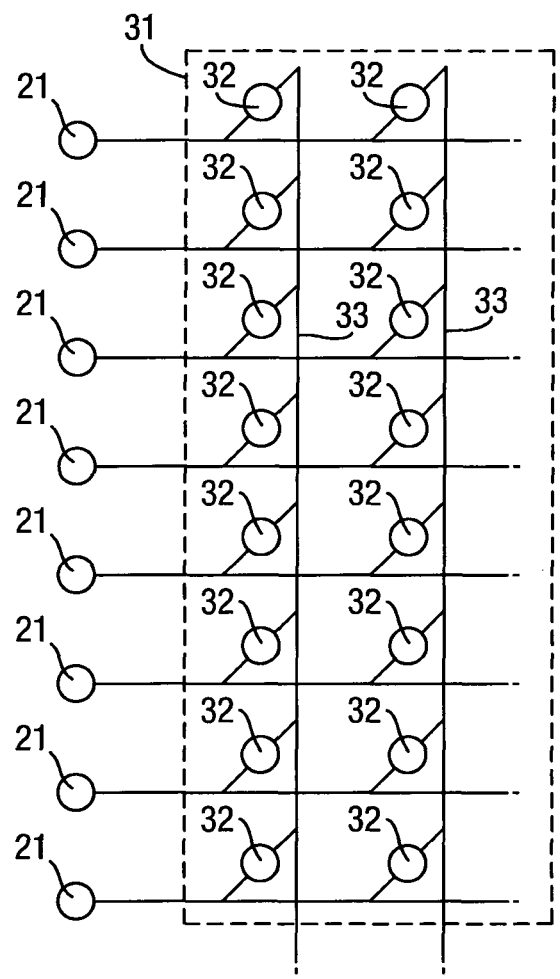

ically complex and expensive, and difficult to scale up. Typically it is desired to detect large numbers of interactions, for example by using an array of sensor elements, but this creates practical and cost penalties.
LIPID BILAYER SENSOR ARRAY

RELATED APPLICATIONS

This application is a 35 U.S.C. §371 national stage filing of PCT Application No. PCT/GB2010/000789 filed on Apr. 19, 2010, which claims priority to U.S. Provisional Application No. 60/170,729 filed Apr. 20, 2009. The contents of the aforementioned applications are hereby incorporated by reference.

The present invention relates to the detection of physical phenomena using sensor elements. Some aspects of the invention have particular application to the detection of stochastic physical events, such as events which involve the interaction of a molecular entity, for example with a membrane protein inserted in a lipid bilayer.

To perform the sensing of molecular entities, it has been disclosed to use membrane proteins inserted in a lipid bilayer. The interaction of the molecular entity with the membrane protein is capable of modulating an electrical signal appearing across the lipid bilayer, for example modulating an ionic current flowing through a membrane protein that is a protein pore. Accordingly, by monitoring an electrical signal appearing across the lipid bilayer to detect changes characteristic of the modulation, it is possible to sense interactions of a molecular entity with the membrane protein. A variety of technologies have been proposed based on this principle, one example being disclosed in WO-2008/102120.

Sensing of molecular entities using this technique provides a method of identifying single molecules and molecular entities directly, without the need for fluorescent labelling and detection. There are a wide range of possible applications, such as sequencing of DNA or other nucleic acids; sensing of chemical or biological molecules for security and defense; detection of biological markers for diagnostics; ion channel screening for drug development; and label-free analysis of interactions between biological molecules.

However, although the basic principles and advantages are well established, there are still technological limitations that make this technique relatively complex and expensive, and difficult to scale up. Typically it is desired to detect large numbers of interactions, for example by using an array of sensor elements, but this creates practical and cost penalties.

A particular constraint is that the electrical signals concerned are very small in magnitude and occur over a very short time, because the interactions involve a single molecular entity. As a result, it is necessary to use a detection circuit that has sufficient sensitivity to amplify an electrical signal from each one of the sensor elements with sufficient time resolution to allow detection of the interaction. Such a detection circuit will typically require a separate detection channel for each sensor element where an interaction is sensed. However, these constraints impact on the cost of the technique.

Thus for many commercial applications, it would be desirable to develop a technique that allows detection of interactions of relatively large numbers of molecular entities using an array of sensor elements, but at relatively low cost. Also for many commercial applications it would be desirable to allow the techniques to be applied to relatively small sample volumes.

Similar issues apply to other techniques for detecting molecular interactions besides the use of membrane proteins in a lipid bilayer, and to other techniques for sensing physical phenomena.

According to a first aspect of the present invention, there is provided a method of sensing a physical phenomenon, the method comprising:

providing a sensor device comprising an array of sensor elements including respective electrodes, each sensor element being arranged to output an electrical signal at the electrode that is dependent on a physical phenomenon with a quality of performance that is variable;

providing a detection circuit comprising a plurality of detection channels each capable of amplifying an electrical signal from one of the sensor elements, the number of sensor elements in the array being greater than the number of detection channels;

providing a switch arrangement capable of selectively connecting the detection channels to respective sensor elements;

controlling the switching arrangement to selectively connect the detection channels to respective sensor elements that have acceptable quality of performance on the basis of the amplified electrical signals that are output from the detection channels.

According to a second aspect of the present invention, there is provided an apparatus for sensing of a physical phenomenon, the apparatus comprising:

a sensor device comprising an array of sensor elements including respective electrodes, each sensor element being arranged to output an electrical signal at the electrode that is dependant on a physical phenomenon, the sensor elements having variable quality of performance;

a detection circuit comprising a plurality of detection channels each capable of amplifying an electrical signal from one of the sensor elements, the number of sensor elements in the array being greater than the number of detection channels;

a switch arrangement capable of selectively connecting the detection channels to respective sensor elements.

a switching controller arranged to control the switching of the switch arrangement to selectively connect the detection channels to respective sensor elements that have acceptable quality of performance on the basis of the amplified electrical signals that are output from the detection channels.

Thus the present invention is based on an appreciation that sensor elements for the detection of certain physical phenomena have variable quality of performance. For example, in the case of detecting the occurrence of a stochastic physical event such as an interaction of a molecular entity with a membrane protein in a lipid bilayer, individual sensor elements might have different quality of performance in the formation of a lipid bilayer or in the number of membrane proteins that insert. This may result in the quality of performance varying in that certain sensor elements are unable to detect the physical event at all or in different sensor elements outputting a signal of differing quality.

The present invention takes advantage of this appreciation by using an array of sensor elements in which the number of sensor elements is greater than the number of detection channels used to amplify the electrical signal. By selectively connecting the detection channels to respective sensor elements it is possible to increase the efficiency with which the detection channels are used. For a given number of detection channels, this increase in efficiency is effectively achieved by providing redundancy in the number of sensor elements included in the array.

The increase in efficiency arises due to the ability to select sensor elements that have acceptable quality of performance, for connection to a detection channel. For example, in the case that of detecting the occurrence of a stochastic physical event that is an interaction of a molecular entity with a membrane protein in a lipid bilayer, inefficiency in the utilisation of the sensor elements typically occurs because of a statistical variation in the number of membrane proteins inserting in the individual lipid bilayers. This statistical variation means that only some sensor elements inevitably have acceptable numbers of membrane proteins inserted therein. The present invention provides an increase in the efficiency of using the detection channels because the detection channels are selectively connected to sensor elements that do have acceptable quality of performance.

In the specific example discussed in more detail below, with even a modest redundancy factor of 4, the peak efficiency can be improved from 36% to over 80%, making much better use of the detection channels.

The detection channels 30 are typically significantly more expensive to produce than the sensor elements. For example in some types of apparatus 1, the sensor device 2 may be sufficiently cheap to be disposable. Accordingly, to achieve a given number of effective detection channels 30, the increase in the efficiency of utilisation of the detection channels leads to a corresponding reduction in the cost of the apparatus as a whole because less detection channels need to be provided. On the basis of the previous example, the same quality of performance of achieving 205 effective detection channels, could be achieved from a detection circuit having 256 detection channels working at 80% efficiency as from a detection circuit having 569 detection channels working at 36% efficiency.

An additional advantage of the present invention is that the redundancy provides a greater degree of tolerance to variations in efficiency of the sensor elements and thereby maintains a more uniform overall efficiency. Similarly, it is also potentially more tolerant of sensor elements whose quality of performance ceases to be acceptable during operation. A sensor whose quality of performance degrades may in fact become damaging to the correct functioning of the sensor array, and may affect not only the detection channel to which it is connected but also other channels. Accordingly, the ability to de-select the sensor, or to isolate it, may be extremely beneficial to the continuing operation of the whole sensor array as well as potentially restoring useful signals to the detection channel in question.

In terms of their electrical function, the switch arrangement and switching controller are similar to those employed in known sensor apparatuses employing time division multiplexing (TDM) in the connection of detection channels to sensor elements, for example in an image sensor. In such known sensor apparatuses, an individual detection channel is connected to successive ones of a group of sensor elements in order to output an amplified output signal from every sensor element of the group in turn. The aim of TDM is to output signals from all sensor elements of an array with a limited number of detection channels. As the outputs of all sensor elements are of interest, such TDM is reliant on the output signals of interest from an individual sensor element having a low bandwidth relative to the TDM period so that features of the output signal occurring when an individual sensor element is not connected to a detection channel are not missed. For example TDM is frequently applied to sensor elements that integrate a signal over the TDM period.

In contrast, the present invention involves the redundant provision of sensor elements whose quality of performance varies. Only one sensor element, selected from a redundant group to have an acceptable quality of performance, is connected to each detection channel. An intrinsic part of the technique to obtain the benefit of increased efficiency is that the output signals of other sensor elements that are not connected to a detection channel is lost. Thus the present invention is applicable to the detection of stochastic physical events that occur in a time period that is shorter than the average period for which a detection channel is connected to a sensor element.

The invention has particular application to the sensing of a stochastic physical event, such as an interaction of a molecular entity, for example with a membrane protein in a lipid bilayer. In this field, it is typically the case that the sensor elements have variable quality of performance that may or may not be acceptable. For example in the case of a sensor element employing a membrane protein in a lipid bilayer, the quality of performance may vary in whether a lipid bilyaer forms and in the number of effective membrane proteins that insert. Conversely, in this field of stochastic sensing, the strict requirements on the sensitivity and time-resolution of the detection channel mean that the advantages of the invention are particularly strong.

The invention also has particular application to sensing using sensor elements which each comprise a respective well formed in a substrate and within which are arranged the respective electrodes.

However, the present invention is generally applicable to sensing of any type of physical phenomenon by an array of sensor elements arranged to output an electrical signal at the electrode that is dependant on a physical phenomenon, where the sensor elements have variable quality of performance. In this context the term "physical" is used to indicate physical phenomena of any type, including phenomena in the fields of chemistry and biochemistry. Indeed the present invention has particular application in these fields.

The sensor element may comprise an ion channel, such as a solid state or biological ion channel. Preferably, it is a biological ion channel, such as a membrane protein ion channel, for example hemolysin.

Biological ion channels will typically be present in a membrane. Generally the membrane will not be that in which the ion channel occurs naturally. The membrane may be a solid state membrane or a biological membrane. Biological membranes include lipid bilayers, which may be anchored to a support structure.

Solid state membranes encompass both organic and inorganic materials, for example microelectronic materials, insulating materials such as $Si_3N_4$, $Al_2O_3$ and SiO, organic and inorganic polymers such as polyamide, plastics such as Teflon™ or elastomers such as two-component addition-cure silicone rubber and glasses.

A solid state membrane may be a layer, such as a film or a coating on a support.

When the physical event is the interaction of a molecular entity with an ion channel, the sensor element may additionally comprise a molecular motor, such as an enzyme, which interacts with the molecular entity before during or after the interaction. Examples of a molecular motor include DNA polymerase, RNA polymerase, exonuclease, helicase, phage motor protein, reverse transcriptase, DNA translocase.

An embodiment of the present invention will now be described by way of non-limitative example with reference to the accompanying drawings, in which.

FIG. 1 is a schematic diagram of an apparatus for sensing interactions of a molecular entities with membrane proteins inserted in lipid bilayers;

FIG. 2 is a cross-sectional view of part of the sensor device of the apparatus;

FIG. 7 is a schematic diagram of the switching arrangement of the detection circuit; and FIG. 8 is a schematic diagram of an alternative form of the switching arrangement of the detection circuit.

Figure 3:
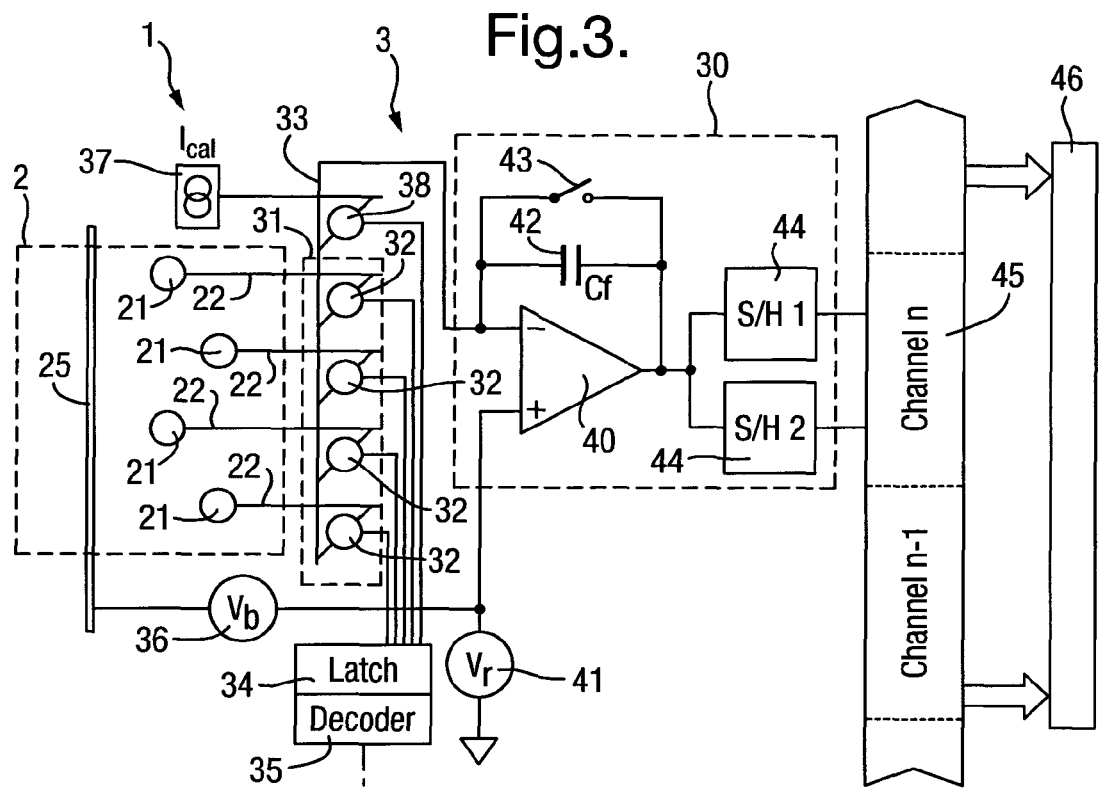
FIG. 3 is a diagram of the detection circuit of the apparatus.
Figure 4:
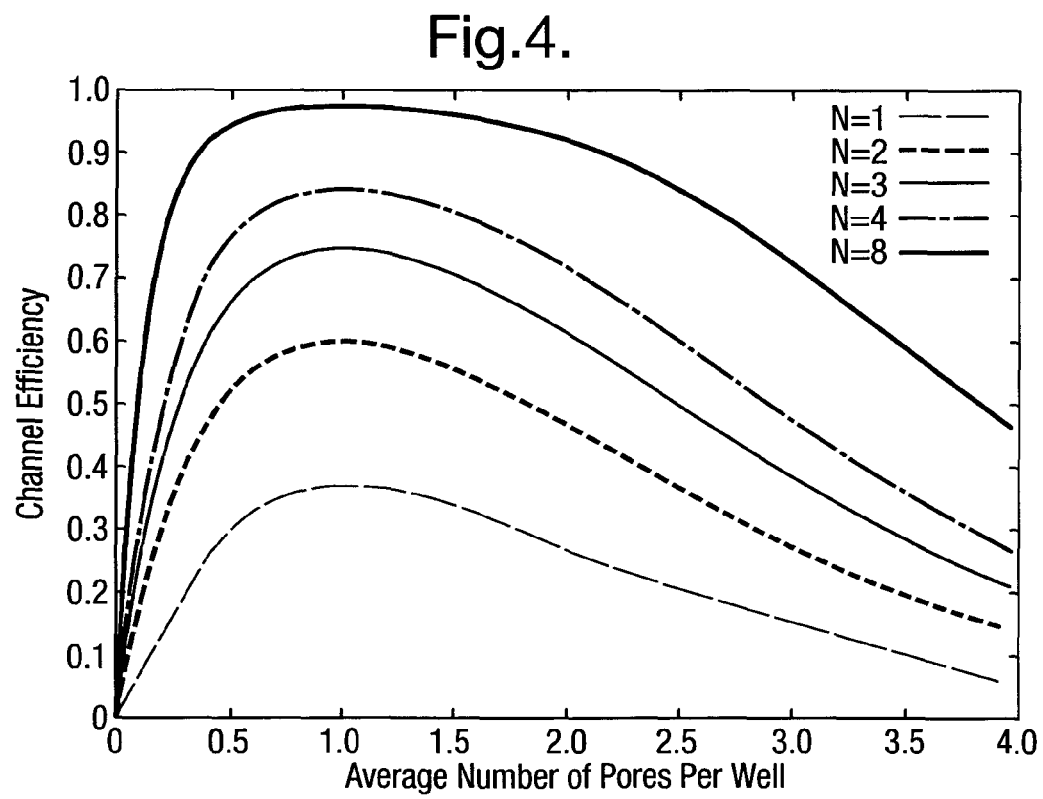
FIG. 4 is a graph of the efficiency of usage of detection channels against the average number of membrane proteins inserted per well for different levels of redundancy in the number of wells.

There will first be described an apparatus 1 for sensing interactions of a molecular entities with membrane proteins inserted in lipid bilayers that is shown schematically in FIG. 1. The apparatus 1 comprises a sensor device 2 connected to a detection circuit 3 which is in turn detected to a data processor 4.

The sensor device 2 is an apparatus as described in detail in International Patent Application No. PCT/GB08/004,127 which is incorporated herein by reference. Without limitation to the generality of the teaching therein, the sensor device 2 has a construction as shown in cross-section in FIG. 2 comprising a body 20 in which there is formed a plurality of wells 21 each being a recess having a well electrode 22 arranged therein. A large number of wells 21 is provided to optimise the data collection rate of the apparatus 1. In general, there may be any number of wells 21, typically 256 or 1024, although only a few of the wells 21 are shown in FIG. 2.

The body 20 is covered by a cover 23 that extends over the body 20 and is hollow to define a chamber 24 into which each of the wells 21 opens. A common electrode 25 is disposed within the chamber 23.

The sensor device 2 is prepared to form a lipid bilayer 26 or layer of other amphiphilic molecules across each well 21 and to insert membrane proteins into the lipid bilayer 26. This preparation is achieved using the techniques and materials described in detail in International Patent Application No. PCT/GB08/004,127, but may be summarized as follows. Aqueous solution is introduced into the chamber 24 to form the lipid bilayer 26 across each well 21 separating aqueous solution in the well 21 from the remaining volume of aqueous solution in the chamber 24. Membrane proteins are provided into the aqueous solution, for example by being introduced into the aqueous solution before or after that is introduced into the chamber 24 or by being deposited on an internal surface of the chamber 24. The membrane proteins spontaneously insert from the aqueous solution into the lipid bilayers 26. Such spontaneous insertion is a dynamic process and so there is a statistical variation in the number of membrane proteins inserted into individual lipid bilayers, typically having a Poisson distribution.

In respect of any given well 21, when a lipid bilayer 26 has been formed and a membrane protein is inserted therein, then the well 21 is capable of being used as a sensor element to sense interactions between molecular entities and the membrane protein that are stochastic physical events because the output electrical signal across the lipid bilayer 26 is dependent on those interactions in that the interactions cause characteristic changes therein. For example in the case that the membrane protein is a protein pore, then there will typically be interactions between the protein pore and a particular molecular entity (analyte) that modulate the flow of ions through the pore, creating a characteristic change in current flow through the pore. The molecular entity may be a molecule or part of a molecule, for example a DNA base. Such interactions are very brief, requiring a high time resolution and continuous monitoring if it is desired to detect each interaction.

However the quality of performance of the wells 21 as sensor elements is variable. The lipid bilayer might not form meaning the well 21 has no performance; although in practice high efficiency of formation is achievable. More significantly, the variation in the number of effective membrane proteins inserting into the lipid bilayer affects the quality of performance. Clearly if no membrane protein inserts the well 21 has no performance. The quality of performance may also be variable with the number of effective membrane proteins inserting. Sometimes there may insert a membrane protein that is not effective for the desired stochastic sensing, for example because it is denatured. In general the number of effective membrane proteins that are acceptable depends on the type of stochastic sensing being performed. In the example below, acceptable quality of performance is the insertion of a single effective membrane protein, with plural membrane proteins being unacceptable. In other situations, insertion of plural effective membrane proteins may be acceptable.

The detection circuit 3 is arranged as shown in FIG. 3 wherein the sensor device 2 is shown schematically. In the sensor device 2, the wells 21 are divided into groups. In FIG. 3, the group consists of four wells 21, but the groups may in general consist of any plural number of wells 21. The detection circuit 3 has a detection channel 30 associated with each group of wells 21. For clarity, FIG. 3 shows a single group of wells 21 and a single detection channel 30 for clarity, but typically there are plural groups of wells 21 each with an associated detection channel 30 arranged as shown in FIG. 3. For example, for some applications, the sensor device 2 might comprise a total of 4096 wells 21 and 1024 detection channels 30.

The apparatus 1 further includes a switch arrangement 31 which is capable of selectively connecting the detection channel 30 to any one of the wells 21 in the group. In particular, the switch arrangement 31 is a 1-to-4 multiplexor (in general a 1-to-N multiplexor where N is the number of wells 21 in the group), comprising four switches 32 each connected between the well electrode 22 one of the wells 21 and a common contact 33 which is itself connected to the input of the detection channel 30.

The switches 32 may in principle be any type of analog switch, but are preferably semiconductor switches, for example formed by transistors, preferably field effect transistors. The switches 32 are selected to provide minimal leakage to the detection channel 30 either from the wells 21 that are not connected through switches 32 that are open or from the latch 34 through the switches 32. Dynamic charge injection effects are avoided by running the apparatus 1 with the switches in a static configuration for most of the time.

The state of the switch arrangement 31 is controlled by data stored in a digital latch 34 controlled by decoder logic 35 which controls the latch 34 in accordance with a control signal received by the decoder logic 35 so that any one single switch 32 is closed at a time, thereby connecting the corresponding well 21 to the detection channel 30. The decoder logic 35 allows the switch arrangement 31 in respect of each group of wells 21 to be switched without affecting the state of the switch arrangement 31 in respect of any other group.

There is no requirement to be able to change the configuration of the switch arrangement 31 rapidly. Typically, changes may be required on a time-scale of minutes and a complete update should be achievable on a timescale of up to 0.1 s to 1 s. It would be acceptable to implement the latch 34 as a shift register and to implement a serial data interface for the decoder logic 35, preferably utilizing differential signalling.

The wells 21 are biased with respect to the input of the detection channel 30 by a bias supply 36 connected to the common electrode 35. Typically the bias voltage is up to −200 mV.

Any well 21 which is not actively connected to the detection channel 30 is allowed to float to the potential of the common electrode 25 via the fluid in the well 21 and will therefore pass no current. This eliminates the potential for amplifier saturation by wells 21 which have no bilayer 26. The decoder logic 35 may also control the latch 34 to provide a state in which all of the switches 32 open, thus allowing all the wells 21 in the group to float. In this state, the detection channel 30 has no input current, and none of the wells 21 passes any current either.

To reduce costs, the detection circuit 3 is implemented in a semiconductor chip provided separately from the sensor device 2. However, as an alternative in principle it would be possible to implement some components of the detection circuit 3, for example the switch arrangement 31, latch 34 and decoder logic 35, into a separate semiconductor chip integrated into the sensor device 2. This might reduce the interconnection requirements, but requires the sensor device 2 to have a few extra digital control lines to supply the control signal to the decoder logic 35.

Optionally, the detection circuit 3 may be arranged as follows to supply a calibration current of known magnitude, equivalent to the current passed by a working well 21, typically of magnitude −50 pA to −100 pA, to the detection channel 30 for testing purposes so that the functionality of the detection circuit 3 can be assured prior to the introduction of any chemistry. The detection circuit 3 includes a calibration source 37 that is operable to supply the calibration current and a further switch 38 connected between the calibration source 37 and the common contact 33. The further switch 38 is controlled by the latch 34 and the decoder logic 35 in the same manner as the switch arrangement 31 to allow connection of the calibration source 37 to the detection channel 30, instead of any of the wells 21.

Each detection channel 30 is arranged as follows to amplify the electrical signals from a well 21 that is connected thereto by the switch arrangement 31. The detection channel 30 is therefore designed to amplify very small currents with sufficient resolution to detect the characteristic changes caused by the interaction of interest. The detection channel 30 is also designed with a sufficiently high bandwidth to provide the time resolution needed to detect each such interaction. These constraints require sensitive and therefore expensive components.

The detection channel 30 includes a charge amplifier 40 that is a differential amplifier having: an inverting input which constitutes the input of the detection channel 30 and is connected to the common contact 33; and a non-inverting input that is connected to an internal reference source 41. The bias source 36 is connected between the common electrode 25 of the sensor device 2 and the non-inverting input of the charge amplifier 40 to apply the bias voltage therebetween.

The charge amplifier 40 is arranged as an integrating amplifier by means of a capacitor 42 being connected between the inverting input of the charge amplifier 40 and the output of the charge amplifier 40. A control switch 43 is connected in parallel with the capacitor 42 to control the integration performed by the charge amplifier 40. The charge amplifier 40 integrates the current supplied thereto from the well 21 to provide an output representative of the charge supplied in each integration period, the integration period being of fixed duration so that they are representative of current, that duration being short enough to provide sufficient resolution for monitoring of events occurring in the well 21 connected thereto.

The output of the charge amplifier 40 is connected to two sample-hold amplifiers 44 arranged in parallel and optionally provided with voltage gain. In use, the sample-hold amplifiers 44 are operated to provide correlated double-sampling by each being switched synchronously with the control switch 43 to sample and hold the output of the integrating charge amplifier 40 at the start and end of each integration period. The useful signal is derived by taking differences between the two outputs of the sample-hold amplifiers 44. The sampling rate is sufficiently high to time resolve the output signals. The amplified signal output by the sample-hold amplifiers 44 are supplied to a multiplexor 45 which multiplexes the amplified signals output by all the detection channels 30 and supplies them to the data processor 4. The multiplexor 45 may be a shift register connected to the data processor 4 through an A/D convertor 46, but in general the multiplexor 45 could take any suitable form, including being a digital device with A/D conversion occurring between the sample-hold amplifiers 44 and the multiplexor 45.

Alternatively each detection channel 30 may be provided with two charge amplifiers arranged in parallel and used alternately to provide greater efficiency by each charge amplifier being reset whilst the other charge amplifier is performing integration.

It is occasionally necessary to un-block a membrane protein that is a protein pore, by inverting the potential applied across the well 21 via the common electrode 25. For this to be effective, the input to the charge amplifier 40 is designed to remain at a constant bias potential even when presented with a negative current (of similar magnitude to the normal current, typically of magnitude −50 pA to −100 pA).

The data processor 4 receives and processes the signals from each detection channel 30 output from the detection circuit 30. The data processor 4 stores and processes the amplified signals.

The data processor 4 also controls the operation of the detection circuit 3 and acts as a switching controller for the switch arrangement 31 by supplying the control signal to the decoder circuit 35. The data processor 4 may be a microprocessor running an appropriate program or may include dedicated hardware. The data processor 4 may comprise a card to be plugged into a computer such as a desktop or laptop. Such a computer may include graphics tools for displaying the amplified signals to the user, and may also provide analysis of the amplified signals depending on the interaction of interest.

In operation, the data processor 4 monitors the amplified signals 40 output by each detection channel 30 and controls the switch arrangement 31 on the basis thereof. In particular, the data processor 4 controls the switch arrangement 31 to connect the detection channel 30 to one of the wells 21 which has acceptable quality of performance, i.e. in this example meaning that there a lipid bilayer 26 is formed across the lipid bilayer with a single membrane protein inserted therein.

To achieve this, the data processor 4 performs a sensor selection process after the sensor device 2 has been prepared by the user, as described above.

In this sensor selection process, the switch arrangement 31 is controlled to connect the detection channel 30 successively to each of the wells 21, in respect of each group. During this process the amplified signal is monitored to determine in respect of each well 21 whether a lipid bilayer is formed and the number of membrane proteins inserted. This may be achieved by analysing the amplified signals to detect signals that are characteristic of the physical state of the well 21, for example using the analysis techniques disclosed in WO 2008/102120 (International Patent Application No. PCT/GB08/000,562) which is incorporated herein by reference. A well 21 having acceptable quality of performance is thereby detected on the basis of the amplified signals.

In the sensor selection process, each well 21 in a group may be tested or the process may stop as soon as a well 21 having acceptable quality of performance is detected. In either case, the switch arrangement 31 is subsequently switched to connect the detection channel 30 to a well 21 having acceptable quality of performance. Thereafter the amplified signal from the well 21 is monitored to allow sensing of events in that well 21.

Ideally each of the detection channels 30 is connected to a well 21 by the switch arrangement 31. However, if no well 21 has acceptable quality of performance, then the switch arrangement 31 may be subsequently switched to disconnect the detection channel 30 from all the wells 21 in the group. In that case, the sensor selection process may be repeated after a predetermined period of time to detect whether the quality of performance of a well 21 has become acceptable subsequently.

The detection channels 30 are connected to a well 21 by the switch arrangement 31 continuously, that is without scanning the detection channels 30 across plural wells 21. This is because of the need to sense events in a well 21 that do not persist. This contrasts with a CMOS light sensor wherein incident light is integrated in sensor elements and amplifiers are successively connected to scanned lines of sensor elements.

Similarly, during subsequent operation, the amplified signal is monitored to detect whether the quality of performance of any given well 21 ceases to be acceptable, for example by a second membrane protein becoming inserted into the lipid bilayer 26 or by an inserted membrane protein separating from the lipid bilayer 26. In this case, the switch arrangement 31 is subsequently switched to connect the detection channel 30 to a different well 21 that has acceptable quality of performance. The different well 21 may a well 21 previously determined to have acceptable quality of performance or may be selected anew by performing a sensor selection process again. The detection channel 30 will then continue to supply useful data, and the efficiency of the apparatus 1 will be restored. However, it is noted that the quality of performance of wells 21 becoming unacceptable is relatively rare. Typically, the quality of performance of the well 21 will remain acceptable for a period sufficient to sense many occurrences of the interaction of interest between the membrane protein and a molecular entity. Accordingly, the average period for which a detection channel 30 is connected to a sensor element is much greater than the time period needed to sense individual events.

The redundancy in the number of wells 21 as compared to the number of detection channels 30 increases the efficiency with which the detection channels 30 are used, as follows.

The insertion of membrane proteins into a lipid bilayer 26 is a random process that follows Poisson statistics. This means that even when the average number of membrane proteins per well 21 is one, a significant number of wells 21 may have none, two or more membrane proteins inserted, and these wells 21 are then not useful. For example, it is found that in a particular embodiment the maximum probability for finding just one membrane protein in a well 21 is about 36%, and this is only achieved if conditions are optimal. A greater or lesser membrane protein concentration quickly results in a reduction of useable wells 21 (especially a lesser exposure). Current estimates for efficiency which is likely to be achieved in practical embodiments are about 20%.

In the absence of redundancy in the number of wells 21, the consequence for an apparatus 1 having 1024 detection channels 30 is that it can only field about 368 working wells 21 at best. The remaining wells 21 and their detection channels 30 are not useable. Similarly, for an apparatus 1 having 128 detection channels 30, the number of wells 21 having acceptable quality of performance is expected to be around 46 at best. To achieve a given number of wells 21 required for a given application, without redundancy it is therefore necessary to provide a device with a large number of detection channels 30. However, as the detection channels 30 are expensive, this is counter-productive in terms of cost and reliability, as well as involving the need to generate and discard large quantities of useless data. However, the redundancy in the number of wells 21 in the apparatus 1 deals with this issue by increasing the efficiency in the usage of the detection channels.

Lipid bilayers 26 are formed with an efficiency which may be assumed to approach 100% for current purposes. Membrane proteins are then inserted using a solution whose concentration and exposure time is adjusted to give a mean number of membrane proteins per well 21 near to one. Because the wells 21 might not in practice have a lipid bilayer 26 of the same size, their capture efficiencies will vary. This combines with Poisson statistics to give a spread in the number of membrane proteins per well 21. The apparatus 1 characterises the sensor device 2 to detect which wells 21 have active, useful membrane proteins.

Taking the number of wells 21 in each group as N, as each detection channel 30 has access to N wells 21 instead of just one well 21, there is a greater chance that one of the N wells 21 will have acceptable quality of performance. At the end of the array characterisation phase, the apparatus 1 can therefore expect to have many more usable wells available. The theory behind this may be understood as follows.

The probability P1 of inserting just one membrane protein into a given well 21 follows a Poisson distribution with a defined mean value which depends upon the area of the lipid bilayer 26, the concentration of membrane proteins in solution and the time for which the lipid bilayers 26 are exposed to the membrane protein solution. The efficiency where each detection channel 30 can access N wells 21 is given by the probability that at least one of the N wells 21 has exactly one membrane protein inserted. If more than one of the N wells 21 has one membrane protein inserted, the apparatus 1 will not be able to gather extra data. The overall efficiency can be calculated from the probability Q that any given well 21 does not have exactly one membrane protein inserted (Q=1−P1). The probability that all of the N wells have other than one membrane protein inserted is simply QN. The probability that at least one well 21 has a single membrane protein inserted is therefore (1−QN).

Based on these probabilities, a simulation has been created to show how the overall efficiency (i.e. proportion of detection channels having a well 21 with acceptable quality of performance) for changes with the average number of membrane proteins per well 21 for different levels of redundancy in the number of wells 21, starting with one well 21 per detection channel 30 (i.e. no redundancy) and rising to 8 wells 21 per channel. The results are shown in FIG. 1 which shows the channel efficiency and FIG. 2 which shows the efficiency gain as compared to there being no redundancy. The first curve (N=1) shows the case where each detection channel 30 can access one well 21 and has a peak efficiency of about 0.36 as stated above. As the number of available wells 21 increases, the efficiency rises. The rise is rapid at first but becomes less marked as the number of wells 21 per channel increases. For example, a redundancy of four wells 21 per detection channel 30 offers a peak efficiency of about 83%.

The increased redundancy also flattens the peaks in the curves slightly, meaning that high efficiency is maintained even if the average number of membrane proteins per well 21 varies by quite a large factor. This conveys some measure of resilience to variability in the system.

Figure 5:
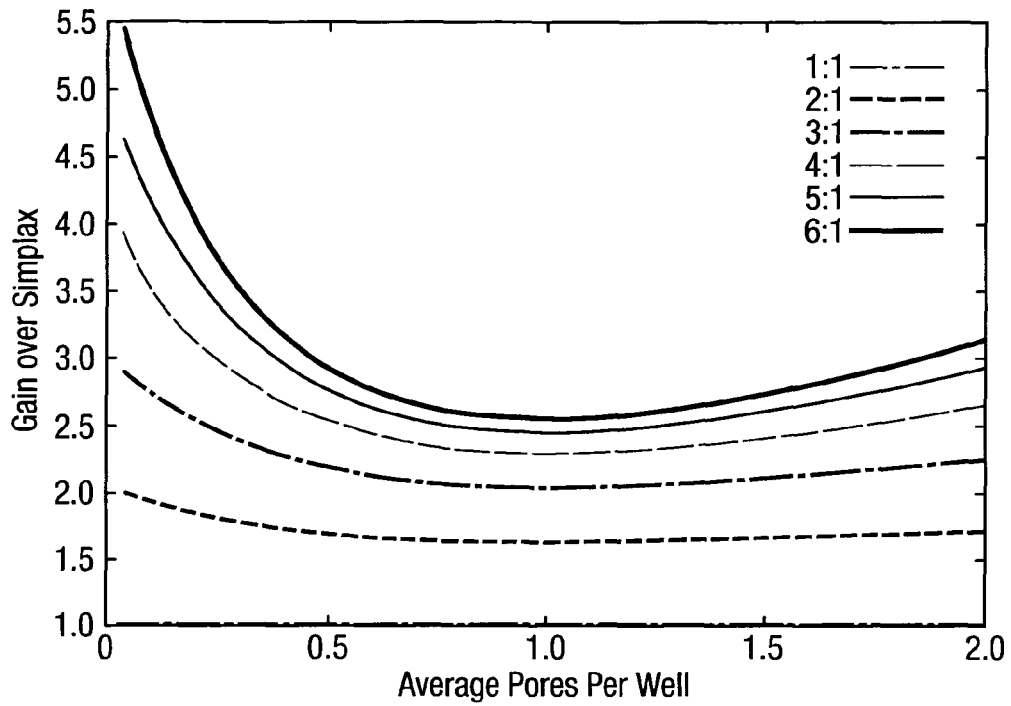
FIG. 5 is a graph the gain in efficiency relative to there being no redundancy against average number of membrane proteins inserted per well for different levels of redundancy.

Although peak efficiency is still obtained at an average of one membrane protein per well 21, the shapes of the curves in FIG. 5 indicate that the redundancy confers a disproportionate advantage when the average number of membrane proteins per well 21 departs from the optimum value, particularly on the low side. The redundancy acts to impart a gain factor that offsets (without completely compensating) the loss of efficiency caused by a decreased average number of membrane proteins per well 21. This is equivalent to imparting greater tolerance to the apparatus 1.

Table 1 shows maximum potential efficiencies as a function of the redundancy factor over a four-fold variation of membrane protein exposure (concentration of membrane protein solution multiplied by time the solution is in contact with the lipid bilayers 26).

TABLE 1

| Pores/Well | Simplex | 2:1 | 3:1 | 4:1 | 5:1 | 6:1 |
| --- | --- | --- | --- | --- | --- | --- |
| 0.5 | 0.31 | 0.51 | 0.66 | 0.76 | 0.84 | 0.89 |
| 1.0 | 0.37 | 0.60 | 0.75 | 0.84 | 0.94 | 0.96 |
| 2.0 | 0.27 | 0.47 | 0.61 | 0.72 | 0.79 | 0.85 |

As the redundancy is increased, the overall efficiency variation as a function of exposure reduces.

Thus, a small amount of redundancy improves the overall efficiency of the apparatus as indicated in the Table 2 which shows number of wells 21 having acceptable quality of performance for different assumed membrane protein insertion efficiencies ("PIE")

TABLE 2

| Detection Channels | PIE 20% 1 well/channel | PIE 36% 1 well/channel | PIE 20% 4 wells/channel | PIE 36% 4 wells/channel |
| --- | --- | --- | --- | --- |
| 128 | 26 | 46 | 75 | 102 |
| 256 | 52 | 92 | 151 | 204 |
| 512 | 104 | 184 | 302 | 408 |
| 1024 | 208 | 368 | 604 | 816 |

The improvement is clearly shown. For example, an apparatus 1 having 512 detection channels 30 with a 2048 wells 21 (four-fold redundancy) is expected to deliver up to 408 wells 21 having acceptable quality of performance under optimum conditions, leaving only about 20% of the amplifier channels inactive. This quality of performance can be contrasted with that expected without redundancy where an apparatus having 1024 detection channels 30 with 1024 wells 21 is expected to deliver only 368 wells 21 having acceptable quality of performance under optimum conditions, this requiring twice as many detection channels 30 for worse quality of performance.

The above embodiment uses a switch arrangement 31 which selectively connects each detection channel 30 to a given group of N wells 21, for example a 1-to-N multiplexor. This is illustrated schematically in FIG. 7, for the example of eight wells 21 arranged in two groups for connection to two detection channels 30. The switching arrangement 31 comprises a switch 32 connected between each well electrode 22 and a common contact 33 in respect of that group to which the well 21 belongs.

As an alternative, in principle there could be used a switch arrangement 31 which selectively connects any of the wells 21 to any of the detection channels 30 to any of the wells 21, for example a cross-bar switch. This is illustrated schematically in FIG. 8, for the example of eight wells 21 arranged for connection to two detection channels 30. The switching arrangement 31 comprises a switch 32 connected between each well electrode 22 and each common contact 33. This would further improve the efficiency gain for a given degree of redundancy. The number of wells 21 exceeds the number of detection channels 30 by a factor which reflects the expected probability of experiencing a well 21 that works, and in principle if this factor is sufficiently high then it is possible to approach 100% efficiency. However, this approach is at the cost of a significant increase in complexity, especially as the number of wells 21 and detection channels 30 increases, as the number of switches 32 required is the product of the number of wells 21 and the number of detection channels 30.

These increases in efficiency provide advantages as follows.

A key point is that the number of detection channels 30 needed to obtain results from a given number of wells 21 required for any given application is reduced. The detection channels 30 are much more complex and expensive to produce than the wells 21 because the detection channels 30 include sensitive electronics whereas the wells 21 are simply recesses formed by a common process. Similarly, fewer connections would be required between the sensor device 2 and the detection circuit 3. Thus the reduction in the number of detection channels 30 reduces the cost of the apparatus 1 as a whole, as well as improving reliability and production yield. The size of the detection circuit 3 is also reduced.

Similarly, the raw data volume transferred from the detection circuit 3 to the data processor 4 is reduced. This reduces bandwidth and increases efficiency of utilisation of the resources of the data processor (including hardware and software resources), which again reduces costs, or for a given availability of processing resource increases the size of sensor device 2 which may be used. There is also an advantage in cases where the sample to be analysed is limited in volume, putting a practical limitation on the number of molecular entities available for interaction. The increase in the efficiency of the usage of the sensor elements means that a greater proportion of the available interactions are detected by the detection circuit. So increasing the number of interactions is important in applications where it is needed to obtain a large amount of data.

Figure 6:
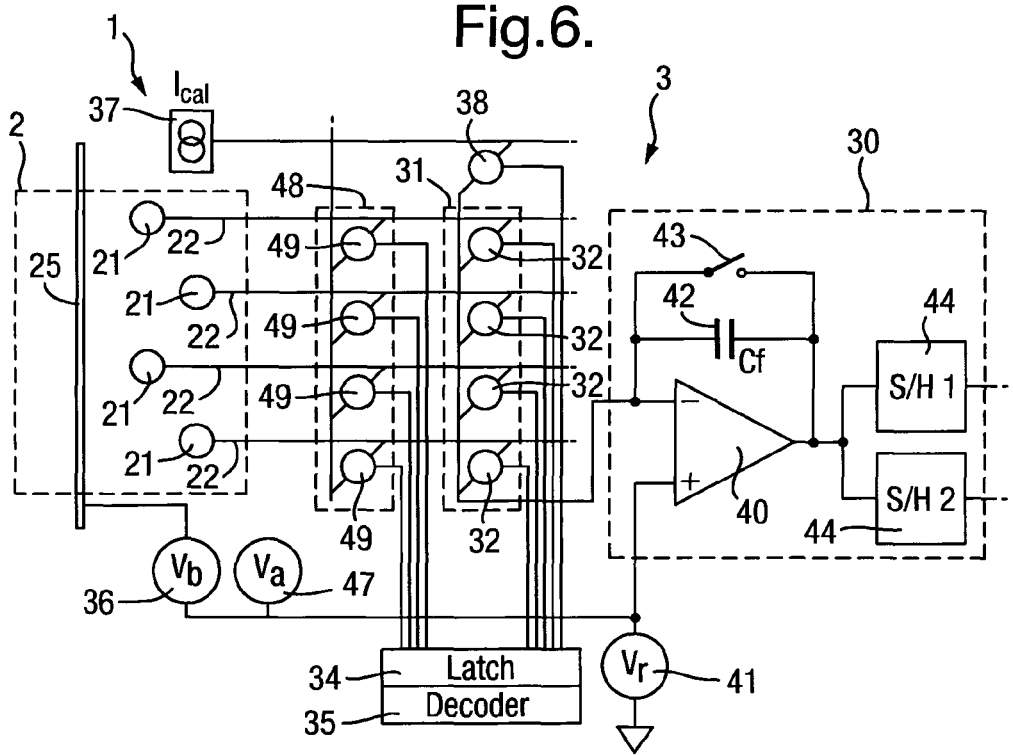
FIG. 6 is a diagram of a modified form of the detection circuit.

There will now be described a modified form of the detection circuit 3 which is shown in FIG. 6. Components common with the detection circuit 3 shown in FIG. 3 are given common reference numerals and for brevity a description thereof is not repeated.

In the detection circuit 3 shown in FIG. 3, unblocking the membrane proteins which are protein pores may be achieved by inverting the reverse bias applied to the common electrode 25. This is effective, but it has the unfortunate side effect of causing temporary data loss on the entire sensor device 2.

The modified form of the detection circuit 30 shown in FIG. 6 provides the functionality of applying an inverted potential across selected sensor wells 21 without affecting other wells 21.

As described above, the common electrode 25 is maintained at a voltage Vb provided by the bias source 36 above the internal reference voltage Vr provided by the internal reference source 41 so that any well 21 which is connected to the detection channel 30 experiences the required forward bias. The switch arrangement 31 allows any or all of the well electrodes 25 to be isolated from the input to the detection channel 30 which allows the well potential to float.

The detection circuit 30 additionally includes an unblocking bias source 47 and a further switch arrangement 48 comprising four switches 49 and having the same construction as the switch arrangement 31 for selectively connecting the output of the unblocking bias source 47 to the well electrode 22 of any one of the wells 21. The further switch arrangement 48 is controlled by the latch 34 and decoder logic 35. The unblocking bias source 47 provides a bias voltage Vu sufficient to unblock a protein pore. To ensure reliable unblocking, this is typically a reverse bias, although that is not in principle essential.

If the data processor 4, whilst monitoring the amplified signals, detects that a protein pore has become blocked, then the data processor controls the switch arrangement 31 to open the switch 32 connected to the blocked protein pore and controls the further switch arrangement 48 to close the switch 49 connected to the well 21 having the blocked protein pore. This places the well electrode 22 of the well 21 concerned under reverse bias, thereby unblocking the protein pore. After a sufficient period to allow such unblocking, the switch 49 is opened to disconnect the reverse bias and the switch 32 is closed to re-connect the detection channel 30 to the well 21 concerned.

The apparatus 1 described above is designed to sense a physical phenomenon which is an interaction of a molecular entity with a membrane protein in a lipid bilayer 26. However the advantages achieved thereby are equally applicable to sensing other physical phenomenon where the quality of performance of the sensor elements is variable. For example similar advantages are achieved in an apparatus for sensing of other types of interaction of a molecular entity, and/or other types of physical event, by an array of sensor elements arranged to sense occurrences of the physical event by outputting an electrical signal at an electrode that is dependent on those occurrences, where the quality of performance of the sensor element is variable. Similar advantages are achieved in an apparatus for sensing using sensor elements which each comprise a respective well formed in a substrate and within which are arranged the respective electrodes.

In the above example, the quality of performance of a well 21 acting as a sensor element is determined to be acceptable or not on the basis of whether or not a single effective membrane protein is inserted in a lipid bilayer across the well 21. However, other measures of quality of performance are appropriate for other types of sensing. Sometimes, the measure of quality of performance will be a simple decision of whether the sensor element is working or not, as in the above example, but in other situations, it may be a quantitative measure of the quality of the output signal, for example the gain or noise associated with a sensor element. As an example in the field of stochastic sensing of an interaction of a molecular entity with a membrane protein in a lipid bilayer, the quality of the output signal may be dependant on the number of membrane proteins inserted (where plural membrane proteins are desirable), on the noise which can vary with several parameters such as the area of the lipid bilayer, or the electrode performance, or on the drift which can vary with parameters such as the electrode performance.

The features defined in the claims may be used together in any combination.

The invention claimed is:

1. A method of sensing an interaction of a molecular entity with a membrane protein in a lipid bilayer or layer of other amphiphilic molecules, the method comprising:
   providing a sensor device comprising an array of sensor elements each arranged to support a lipid bilayer or layer of other amphiphilic molecules in which a membrane protein is capable of insertion and including respective electrodes, each sensor element being arranged to output an electrical signal at the electrode that is dependent on an interaction of a molecular entity with a membrane protein in the lipid bilayer or layer of other amphiphilic molecules with a quality of performance that is variable depending on whether a membrane is formed and on the number of membrane proteins inserted;
   providing a detection circuit comprising a plurality of detection channels each capable of amplifying an electrical signal from one of the sensor elements, the number of sensor elements in the array being greater than the number of detection channels;
   providing a switch arrangement capable of selectively connecting the detection channels to respective sensor elements;
   controlling the switching arrangement to selectively connect the detection channels to respective sensor elements in respect of which a lipid bilayer or layer of other amphiphilic molecules is formed and an acceptable number of effective membrane proteins on the basis of the amplified electrical signals that are output from the detection channels.

2. A method according to claim 1, further comprising sensing the occurrence of a stochastic physical event in the interaction of a molecular entity with a membrane protein in a lipid bilayer or a layer of other amphiphilic molecules.

3. A method according to claim 1, wherein said step of controlling the switching arrangement comprises controlling the switching arrangement to selectively connect the detection channels to respective sensor elements for a period that is greater than the time period needed to sense an individual event.

4. A method according to claim 1, wherein said step of controlling the switching arrangement comprises controlling the switching arrangement to selectively connect the detection channels continuously to respective sensor elements in respect of which the lipid bilayer or layer of other amphiphilic molecules is formed and an acceptable number of effective membrane proteins are inserted.

5. A method according to claim 1, wherein said step of controlling the switching arrangement comprises controlling the switching arrangement to selectively connect all of the detection channels to respective sensor elements in respect of which the lipid bilayer or layer of other amphiphilic molecules is formed and an acceptable number of effective membrane proteins are inserted.

6. A method according to claim 1, wherein said step of controlling the switching arrangement comprises controlling the switching arrangement to selectively disconnect detection channels from respective sensor elements in respect of which the lipid bilayer or layer of other amphiphilic molecules is formed and an acceptable number of effective membrane proteins are inserted and to re-connect disconnected detection channels to different respective sensor elements in respect of which the lipid bilayer or layer of other amphiphilic molecules is formed and an acceptable number of effective membrane proteins are inserted.

7. A method according to claim 1, wherein the sensor elements each comprise a respective well formed in a body and within which are arranged the respective electrodes.

8. An apparatus for sensing interaction of a molecular entity with a membrane protein in a lipid bilayer or layer of other amphiphilic molecules, the apparatus comprising:
- a sensor device comprising an array of sensor elements each arranged to support the lipid bilayer or layer of other amphiphilic molecules in which a membrane protein is configured for insertion including respective electrodes, each sensor element being configured to output an electrical signal at the respective electrode that is dependant on an interaction of a molecular entity with the membrane protein in the lipid bilayer or layer of other amphiphilic molecules, the sensor elements being configured to have a quality of performance that is variable depending on whether a membrane is formed and on the number of membrane proteins inserted;
- a detection circuit comprising a plurality of detection channels each configured to amplify an electrical signal from one of the sensor elements, the number of sensor elements in the array being greater than the number of detection channels;
- a switch arrangement configured to selectively connect the detection channels to respective sensor elements; and
- a switching controller configured to control the switching of the switch arrangement to selectively connect the detection channels to respective sensor elements in respect of which the lipid bilayer or layer of other amphiphilic molecules is formed and an acceptable number of effective membrane proteins are inserted on the basis of the amplified electrical signals that are output from the detection channels.

9. An apparatus according to claim 8, wherein the switching controller is arranged to control the switching arrangement to selectively connect the detection channels to respective sensor elements for a period that is greater than the time period needed to sense an individual event.

10. An apparatus according to claim 8, wherein the switching controller is arranged to control the switching arrangement to selectively connect the detection channels continuously to respective sensor elements in respect of which the lipid bilayer or layer of other amphiphilic molecules is formed and an acceptable number of effective membrane proteins are inserted.

11. An apparatus according to claim 8, wherein the switching controller is arranged to control the switching arrangement to selectively connect all of the detection channels to respective sensor elements in respect of which the lipid bilayer or layer of other amphiphilic molecules is formed and an acceptable number of effective membrane proteins are inserted.

12. An apparatus according to claim 8, wherein the switching controller is arranged to control the switching arrangement to selectively disconnect detection channels from respective sensor elements that cease to have the lipid bilayer or layer of other amphiphilic molecules formed and an acceptable number of effective membrane proteins inserted and to re-connect disconnected detection channels to different respective sensor elements that do have the lipid bilayer or layer of other amphiphilic molecules formed and an acceptable number of effective membrane proteins inserted.

13. An apparatus according to claim 8, wherein the sensor elements each comprise a respective well formed in a body and within which are arranged the respective electrodes.

14. An apparatus according to claim 8, wherein the switching controller is arranged, after selectively connecting a detection channel to a respective sensor element, to monitor the amplified electrical signals that are output from the detection channel to determine if the sensor element ceases to have the lipid bilayer or layer of other amphiphilic molecules formed and an acceptable number of effective membrane proteins inserted, and in that event to selectively connect the detection channel to a different sensor element that does have the lipid bilayer or layer of other amphiphilic molecules formed and an acceptable number of effective membrane proteins inserted on the basis of the amplified electrical signals that are output from the detection channel.

15. An apparatus according to claim 8, wherein the switch arrangement comprises a plurality of switch elements each arranged to selectively connect one of the detection channels to any sensor element in a predetermined group of sensor elements.

16. An apparatus according to claim 15, wherein the switch elements are N-way multiplexors, the predetermined group containing N sensor elements.

17. An apparatus according to claim 8, wherein the switch arrangement comprises a plurality of switch elements arranged to selectively connect any one of the detection channels to any one of the sensor elements.

18. An apparatus according to claim 8, wherein the detection channels each include an integrating amplifier circuit and a sample-and-hold circuit connected to the output of the integrating amplifier circuit.

19. An apparatus according to claim 8, wherein the sensor device further comprises a common electrode common to all the sensor elements.

20. An apparatus according to claim 8, wherein the apparatus further comprises: a bias source; a further switch arrangement capable of selectively connecting the bias source to any one of the sensor elements.

* * * * *